US012766168B2

(12) United States Patent
Nieuwdorp et al.

(10) Patent No.: US 12,766,168 B2
(45) Date of Patent: Oct. 20, 2026

(54) FECAL MATTER FOR TREATMENT OF CACHEXIA

(71) Applicants: Academisch Medisch Centrum, Amsterdam (NL); Wageningen Universiteit, Wageningen (NL)

(72) Inventors: Max Nieuwdorp, Amsterdam (NL); Willem Meindert De Vos, Amsterdam (NL)

(73) Assignees: Academisch Medisch Centrum, Amsterdam (NL); Wageningen Universiteit, Wageningen (NL)

( * ) Notice: Subject to any disclaimer, the term of this patent is extended or adjusted under 35 U.S.C. 154(b) by 708 days.

(21) Appl. No.: 17/999,538

(22) PCT Filed: Jun. 14, 2021

(86) PCT No.: PCT/EP2021/065909

§ 371 (c)(1),
(2) Date: Nov. 21, 2022

(87) PCT Pub. No.: WO2021/254937

PCT Pub. Date: Dec. 23, 2021

(65) Prior Publication Data

US 2023/0201271 A1 Jun. 29, 2023

(30) Foreign Application Priority Data

Jun. 19, 2020 (NL) ...................................... 2025863

(51) Int. Cl.

*A61K 35/38* (2015.01)
*A61K 9/00* (2006.01)
*A61K 35/00* (2006.01)
*A61K 45/06* (2006.01)
*A61P 3/04* (2006.01)

(52) U.S. Cl.

CPC ............ *A61K 35/38* (2013.01); *A61K 9/0053* (2013.01); *A61K 45/06* (2013.01); *A61P 3/04* (2018.01); *A61K 2035/11* (2013.01)

(58) Field of Classification Search

None
See application file for complete search history.

(56) References Cited

FOREIGN PATENT DOCUMENTS

| | | | |
|---|---|---|---|
| JP | 2018-521013 | A | 8/2018 |
| WO | 2014121298 | A2 | 8/2014 |
| WO | 2016196605 | A1 | 12/2016 |
| WO | 2019/191390 | A2 | 10/2019 |
| WO | 2019171012 | A1 | 9/2022 |

OTHER PUBLICATIONS

Search Report and Written Opinion for Netherlands Application No. NL2025863, dated Feb. 11, 2021, 10 pages.
International Search Report for International Application No. PCT/EP2021/065909, mailed Dec. 23, 2022, 3 pages.
International Written Opinion for International Application No. PCT/EP2021/065909, mailed Dec. 23, 2022, 8 pages.
Bindels et al, "Synbiotic approach restores intestinal homeostasis and prolongs survival in leukaemic mice with cachexia", The I S M E Journal: Multidisciplinary Journal of Microbial Ecology,vol. 10, No. 6, Nov. 27, 2015 (Nov. 27, 2015), p. 1456-1470.
Fearon, et al. "Definition of cancer cachexia□: effect of weight loss , reduced food intake, and systemic inflammation on functional status and. Prognosis" Am J Clin Nutr 2006;83:1345-1350 (Jun. 2006).
Genton et al, "Targeting the Gut Microbiota to Treat Cachexia", Frontiers in Cellular and Infection Microbiology,vol. 9, Sep. 12, 2019 (Sep. 12, 2019), XP055667026.
Haitao et al, "The gut microbiota attenuates muscle wasting by regulating energy metabolism in chemotherapy-induced malnutrition rats", May 15, 2020 (May 15, 2020), vol. 85, No. 6, p. 1049-1062.
Norman et al. "The bioimpedance phase angle predicts low muscle strength, impaired quality of life, and increased mortality in old patients with cancer" J. Am. Med. Dir. Assoc. 16, 173.e17-173.e22 (Feb. 2015).
Turnbaugh et al, "An obesity-associated gut microbiome with increased capacity for energy harvest", Nature, MacMillan Journals Ltd, London,vol. 444, No. 7122, Dec. 1, 2006 (Dec. 1, 2006), p. 1027-1031, XP002492885.
World Health Organization "Towards a Common Language for Functioning , Disability and Health ICF" Int. Classif. 1149, 1-22 (Jan. 2002).
Prado et al. "Prevalence and clinical implications of sarcopenic obesity in patients with solid tumors of the respiratory and gastrointestinal tracts: a population-based study" Lancet Oncol. vol. 9, Issue 7, Jul. 2008, pp. 629-635.
Pusuroglu, et al. "A comparative analysis of leukocyte and leukocyte subtype counts among isolated systolic hypertensive, systo-diastolic hypertensive, and non-hypertensive patients" Kardiologia Polska 2014; 72, 8: 748-754; DOI: 10.5603/KP.a2014.0044.
Decision to Grant a Patent received for Japanese Patent Application No. 2022-577367, mailed on Jan. 13, 2026, 6 pages (2 pages of English Translation and 4 pages of Original Document).
Yu et al. "Fecal microbiota transplantation for the improvement of metabolism in obesity: The FMT-TRIM double-blind placebo-controlled pilot trial" PLoS Med., vol. 17, No. 3, 2020, pp. 1-19 (Mar. 9, 2020).

(Continued)

*Primary Examiner* — Michael V Meller
(74) *Attorney, Agent, or Firm* — TraskBritt

(57) ABSTRACT

The use of allogenic fecal matter for the treatment of cachexia and/or cancer, wherein the allogenic fecal matter is obtained from at least one donor subject, wherein the at least one donor subject has a Body Mass Index (BMI) of at least 30 kg/m2, a HOMA-IR value below 2.5 mg/dL and/or an age below 60 years. Fecal matter from the at least one donor subject may be used to treat cancer and/or related conditions.

15 Claims, 10 Drawing Sheets

(56) References Cited

OTHER PUBLICATIONS

Japanese Notice of Reasons for Refusal for Japanese Application No. 2022-577367, dated Nov. 11, 2024, 11 pages with English translation.
Parenteral and Enteral Nutrition, 2011, vol. 26, No. 5, pp. 1221-1225.

FECAL MATTER FOR TREATMENT OF CACHEXIA

CROSS-REFERENCE TO RELATED APPLICATIONS

This application is a national phase entry under 35 U.S.C. § 371 of International Patent Application PCT/EP2021/065909, filed Jun. 14, 2021, designating the United States of America and published as International Patent Publication WO 2021/254937 A1 on Dec. 23, 2021, which claims the benefit under Article 8 of the Patent Cooperation Treaty to Netherlands Patent Application Serial No. 2025863, filed Jun. 19, 2020.

TECHNICAL FIELD

This application relates to use of fecal matter for the treatment of cachexia, in particular, cancer-associated cachexia.

BACKGROUND

Cancer is a group of diseases wherein body cells grow abnormally leading to the formation of tumors. Unlike benign tumors, tumors caused by cancer are malignant and have the potential to metastasize and/or spread to other parts of the body. Cancer is a form of neoplasia, wherein cell growth is not coordinated with surrounding healthy tissue. Cancer cells are able to grow indefinitely and avoid programmed cell death. Survival rates heavily depend on the type of cancer, the time when it is diagnosed and the availability of curative treatment.

Patients diagnosed with cancer often receive various types of curative treatment, which can be divided into local treatments, including surgery and radiation therapy, and systemic treatments, including immunotherapy, targeted therapy, and chemotherapy. Another type of treatment for patients diagnosed with cancer is palliative care. This type of treatment aims to reduce distress and improve the quality of life of cancer patients. Palliative care for cancer patients is most often, but not exclusively, associated with end stage cancer, wherein the cancer cannot be cured and is expected to result in death of the patient. Palliative care can be combined with curative treatment.

Curative cancer treatment and palliative cancer treatment can be complicated by cachexia, a complex syndrome causing loss of muscle mass. Cachexia is also known as wasting syndrome and can be caused by diverse medical conditions but is most often associated with end-stage cancer, known as cancer cachexia. Unlike sarcopenia, which is a condition characterized by loss of skeletal muscle mass and function, cachexia cannot be treated by administering correct and sufficient nutrition. Cachexia is particularly prevalent in patients diagnosed with gastro-intestinal cancer and pancreatic cancer. Four out of five of all terminal or end-stage cancer patients, suffer from cachexia. Cachexia in cancer patients lowers their quality of life and is associated with increased mortality.

Herremans et al, (2019, Int J Mol Sci) discloses that the imbalance of gut microbiota, known as dysbiosis, has been shown to influence cancer cachexia. The phenotype of cancer cachexia is associated with decreased levels of Lactobacillaceae and increased levels of Enterobacteriaceae and *Parabacteroides.*

WO 2016/196605 A1 discloses a method of treatment and/or prevention of cancer by manipulation of commensal microbiota (also known as microflora). In particular, the amount, identity, presence and/or ratio of microbiota (e.g., gut microbiota) in a subject is manipulated to facilitate one or more co-treatments.

WO 2014/121298 A2 discloses administration to a subject of a therapeutic composition comprising a purified population of spore-forming bacteria produced by providing a fecal material and subjecting the material to a treatment step resulting in purification of spore-forming bacteria.

WO 2019/171012 A1 discloses a stool collection method and sample preparation method for transplanting fecal microbiota. The obtained homogeneous mixture of fecal microbiota may be used for treating intestinal dysbiosis and for treating pathologies associated with such dysbiosis.

The aforementioned methods leave room for improvement in treating cancer and conditions associated therewith, in particular, cachexia. There remains a need to develop a new or improved treatment strategy to improve the quality of life of patients, increase their life expectancy, reduce side effects of treatment, reduce disease complications and/or enhance the response to treatment.

BRIEF SUMMARY

The effects on recipient cancer patients of either Fecal Matter Transplants (FMT) from autologous (own) source or FMT from allogenic donors were investigated, wherein the allogenic donors had varying values for Body Mass Index (BMI), HOMA-IR, and age, while having or not having metabolic syndrome.

The effects of the allogenic FMT on conditions that may be associated with cancer were investigated, in particular, cachexia. The conditions may be caused by the underlying cancer or may be the result of treatment of the cancer.

Surprisingly, it was found that the use of allogenic fecal matter obtained from at least one donor subject having a Body Mass Index (BMI) of at least 30 kg/m$^2$; and/or a HOMA-IR value of at most 2.5 mg/dL and/or an age of at most 60 years leads to prolonged overall survival, increased Progression-Free Survival (PFS), better response to treatment (e.g., chemotherapy) or reduced toxicity/side effects thereof, and/or improved quality of life, in the treatment of cancer or cachexia, and in comparison with autologous FMT, but also in comparison to donors having a lower BMI and/or a higher HOMA-IR value and/or a higher age.

The PFS of cancer associated cachexia patients at 6 months after receiving the allogenic FMT was found to be approximately doubled as compared to patients receiving autologous FMT. In addition, the use may lead to reduction of (cancer associated) symptoms or complications, and/or reduction of (cancer) therapy associated symptoms or complications.

Increased body weight or increased BMI of the recipients receiving the allogenic fecal matter was not observed in comparison with recipients receiving autologous fecal matter, nor in comparison with recipients receiving allogenic fecal matter from donors having a BMI below 30 kg/m$^2$ and/or a HOMA-IR value above 2.5, and/or an age above 60 years.

DETAILED DESCRIPTION

Figure 1:
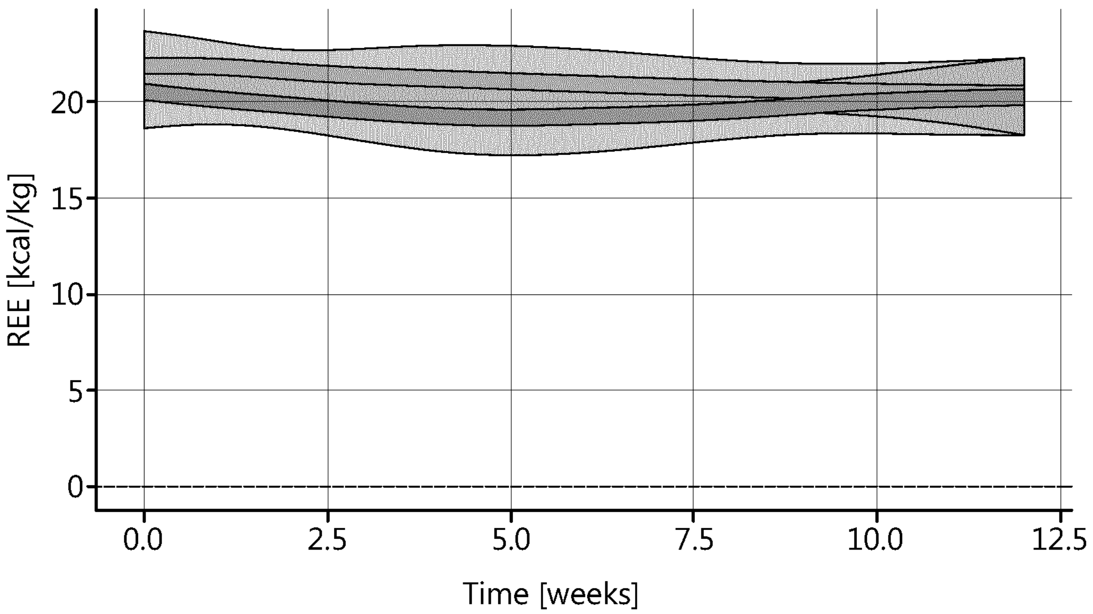
FIG. 1: Mean resting energy expenditures (REE) of all subjects receiving allogenic fecal matter transplantation (FMT) (line with highest REE at time 0) and of all subjects receiving autologous FMT (line with lowest REE at time 0). The shaded areas indicate standard deviations of the mean.

The disclosure relates to the use of allogenic fecal matter for the treatment of cachexia and/or cancer, in particular, cancer associated cachexia, wherein the allogenic fecal matter is obtained from at least one donor subject, such as at least 2, 3, 4 donor subjects, wherein the at least one donor subject has a Body Mass Index (BMI) of at least 30 kg/m$^2$, and/or a HOMA-IR value of at most 2.5 mg/dL and/or an age of at most 60 years.

Accordingly, the disclosure relates to a method of treating cachexia or cancer, in particular, cancer associated cachexia, comprising administering allogenic fecal matter as described herein, to a patient in need thereof.

The treatment can markedly increase overall survival, Progression-Free Survival (PFS), response to (chemo) therapy, quality of life, and/or reduce toxicity/side effects of (chemo) therapy.

Survival time is the time between diagnosis of the disease and the time of death of the patient. Progression-free survival (PFS) is the length of time a patient lives with a disease during and after the treatment of this disease, while the disease does not progress. Progression of a disease is the growth, spread, or deterioration of the disease. Progression can continue until organ failure or death of the patient occurs. PFS is thus indicative of the effectiveness of treatment as the (progression of the) disease is (temporarily) halted.

The treatment according to the disclosure preferably is not for increasing body weight and/or for increasing BMI. Transplantation of allogenic fecal matter according to the present disclosure typically does not result in an increase of body weight and/or BMI of the recipient.

According to another aspect, the treatment according to the disclosure is for improving quality of life, preferably for reducing disease associated symptoms or complications and/or for reducing (cancer) treatment associated symptoms or complications. Surprisingly, the quality of life is greatly increased by transplanting allogenic fecal matter according to the disclosure.

Quality of life (QOL) as used herein denotes the extent to which objective human needs are fulfilled in relation to personal or group perceptions of subjective well-being. A change in QOL can be quantified by comparing at least two responses to the same questions about happiness, life satisfaction, utility, and/or welfare at different points in time.

The term "donor" as used herein denotes a subject who donates fecal matter. The fecal matter according to the present disclosure is thus derived from the donor and may be administered to a recipient. The term "allogenic" as used herein denotes that the fecal matter is not the fecal matter of the patient, but is rather derived from another subject, e.g., of the same species. Optionally after processing, the fecal matter is administered to the patient. Allogenic is the opposite of "autologous," the latter denoting that the fecal matter is the subject's own fecal matter, i.e., obtained from and administered, optionally after processing, to the same subject.

The term "Body Mass Index" or "BMI" as used herein denotes a value derived from dividing the mass of a person by the square of the person's body height, expressed in kg/m$^2$. Donors having a BMI above 30 kg/m$^2$ are typically classified as obese. Preferably the at least one donor subject has an (average) Body Mass Index (BMI) of at least 31 kg/m$^2$, more preferably an (average) BMI of at least 32 kg/m$^2$, even more preferred an (average) BMI of at least 33 kg/m$^2$, and most preferred an (average) BMI of at least 34 kg/m2. Fecal matter of these donor subjects enhances progression-free survival and increases the overall survival time of cancer patients receiving FMT using this fecal matter.

The term "HOMA-IR" as used herein is an abbreviation of Homeostatic Model Assessment for Insulin Resistance. "HOMA-IR" denotes a value, which represents an estimation for insulin resistance, derived from dividing Insulin and Glucose levels in the blood of a person. The HOMA-IR value can be calculated by the following equation:

$$H = \frac{\text{Glucose} \times \text{Insulin}}{405}$$

wherein H is the HOMA-IR value expressed in mg/dL, Glucose represents fasting glucose levels in the blood expressed in mmol/L, Insulin represents fasting insulin levels in the blood expressed in mIU/L. IU (relating to enzyme activity) is an abbreviation of International Units, also called enzyme units. Enzyme activity is the amount of substrate converted per unit of time. One IU equals the conversion of one μmol of substrate per minute.

Preferably, and in line with the foregoing, the at least one donor subject has a HOMA-IR value below 3.0, 2.9, 2.8, 2.7, 2.6, 2.5 or below 2.4, 2.3, 2.2, 2.1 or 2.0 mg/dL, preferably a HOMA-IR value below 1.9, 1.8, or 1.7 mg/dL, more preferably a HOMA-IR value below 1.6, 1.5, 1.4, 1.3, 1.2, or 1.1 mg/dL, and most preferred a HOMA-IR value below 1.0. It was found that fecal matter obtained from these donors increased the number of positive responders (i.e., cancer patients wherein the cancer stabilized or did not progress).

Alternatively or at the same time, the at least one donor subject preferably has an age of at most 60, 59, 58, 57, 56, 55, 54, 53, 52, 51, 50, more preferably an age of at most 49, 48, 47, 46, 45, 44, 43, 42, 41, even more preferably an age of at most 40, 39, 38, 37, 36, 35 years, yet more preferably an age of at most 34, 33, 32, 31, 30 years, most preferred an age of at most 29, 28, 27, 26, 25 years. Younger people often have a relatively low HOMA-IR value. It was considered that fecal matter derived from donors aged at most e.g., 60, 50, or 40 years, is more effective in the treatment of cancer as compared to fecal matter obtained from donors who are older. The gut microbiota is a hugely complex consortium of microorganisms that varies between individuals and with time. The age of the fecal matter of the donor thus appears to influence the effectiveness of allogenic fecal matter on the progress of cancer and related conditions. It is known that the microbiota of seniors deviates from that of younger donors, see e.g., Biagi et al. (*PLoS One.* 2010 May 17; 5(5):e10667).

Preferably, the at least one donor subject according to the present disclosure does not have metabolic syndrome. The absence of metabolic syndrome in donor subjects can further improve the effectiveness on the treatment using fecal matter from such donor subjects, as overall survival can be further prolonged, PFS can be further enhanced, side effects of (cancer) treatment and disease complications can be further reduced, and the quality of life of cachexia or cancer patients can be enhanced. Metabolic syndrome is present in about 50% of people classified as obese based on their BMI. Surprisingly, by excluding people with metabolic syndrome from the group of donors, the above-mentioned improvements can be observed. Exclusion of donors having metabolic syndrome did not appear to have an effect on insulin resistance or insulin sensitivity of FMT recipients.

A person can be considered as having metabolic syndrome if a cluster of three out of five interconnected medical conditions appear together. According to the National Cholesterol Education Program (NCEP) Adult Treatment Panel III (ATP III) definition, and as used herein, metabolic syndrome is present if three or more of the following five criteria are met:

Waist circumference over 40 inches, or 102 cm (men) or over 35 inches, or 89 cm (women);

Blood pressure over 130/85 mmHg;

Fasting triglyceride (TG) level over 150 mg/dL;

Fasting high-density lipoprotein (HDL) cholesterol level below 40 mg/dL (men) or below 50 mg/dL (women); and Fasting blood sugar level over 100 mg/dL.

To measure fasting blood sugar (glucose) levels, fasting triglyceride levels, and fasting high-density lipoprotein cholesterol levels in the blood of a subject, blood is drawn from the subject after the subject has not eaten nor drank anything but water for at least 8 hours. The skilled person is familiar with the methods used to quantify these levels.

The at least one donor subject can be further selected by, in addition to having a Body Mass Index (BMI) of at least 30 kg/m$^2$, a HOMA-IR value of at most 2.5 mg/dL, and/or an age of at most 60 years, by having a thickness of a supraspinal skinfold of at most 40, 39, 38, 37, 36 mm, preferably at most 35, 34, 33 mm, more preferably at most 32, 31, 30 mm, most preferred at most 29, 28, 27, 26, 25 mm. Transplantation of fecal matter from donors having such a supraspinal skinfold thickness may further increase (PFS), and may result in a better response to chemotherapy, reduced toxicity/side effects of chemotherapy, and/or improved quality of life, and prolonged overall survival of cancer patients. A preferred thickness of the supraspinal skinfold of the at least one donor subject can thus range between 14 to 36 mm, such as 16 to 34 mm, or 18 to 32 mm, or 20 to 30 mm, or 22 to 28 mm, or 24 to 28 mm.

Supraspinal skinfold thickness is measured at the supraspinal skinfold site, which is also known as the suprailiac site. The supraspinale skinfold site is the site at the intersection of two lines: (1) the line from the iliospinal to the anterior axillary border and (2) the horizontal line at the level of the iliocristale. The iliospinal is the most inferior or undermost part of the tip of the anterior superior iliac spine (ASIS). The iliocristale is the point on the iliac crest where a line drawn from the midacilla (middle of the armpit), on the longitudinal axis of the body, meets the ilium.

Skinfold calipers can be used to take skinfold measurements and determine the thickness of skin at this site. Calipers is a device usable to measure a distance between opposing sites of an object. Usually, the measurement is performed at the right side of the body. By pulling out and holding ("pincing") the skin at the supraspinale skinfold site, a double layer of skin and underlying adipose tissue is created having an outer end and a longitudinal direction approximately parallel to the waist to head direction of the measured subject. Calipers are applied 1 cm below the outer end of the double skin layer and in an angle perpendicular to a longitudinal direction of the skinfold. Two seconds after the skinfold is pinced using the calipers, a reading in millimeters (mm) is taken. A supraspinale skinfold thickness is calculated as a mean value of two such skin fold measurements and the associated readings.

Alternatively or at the same time, a thickness of a subscapular skinfold of the at least one donor subject preferably is at most 45, 44, 43, 42, 41, or 40 mm, preferably at most 39, 38, 37, 36, or 35 mm, more preferably at most 34, 33, 32, 31, or 30 mm, most preferred at most 29, 28, or 27 mm, such as 17 to 35 mm. A subscapular skinfold measurement can be taken at the subscapular skinfold site, the site 2 cm (0.8 inches) along a line running laterally and obliquely downward from the subscapulare at a 45° angle when the donor subject is standing upright, in a similar manner as described above for the supraspinale skinfold thickness. The subscapulare is the undermost tip of the inferior angel of the scapula Other types of skinfold sites can be used for the current disclosure and are for described in Applied Anatomy and Biomechanics in Sport, second edition, 2009, by T. R. Ackland, B. Elliott, and J. Bloomfield. Skinfold sites include, but are not limited to: triceps skinfold site, the posterior part of the triceps, in the midline, at the level of the midacromiale-radiale landmark; biceps skinfold site, the most anterior part of the biceps at the level of the midacromiale-radiale landmark; abdominal skinfold site, the site 5 cm (2 inches) to the right of the midpoint of the navel or umbilicus; the medial calf skinfold site, the site on the most medial aspect of the calf at the level of the maximal girth; and the front thigh skinfold site, the site equidistant from the inguinal fold and the anterior patella, on the midline of the thigh. Wherein the acromiale is the point at the most superior and lateral border of the acromion process when the subject stands erect with arms relaxed and hanging vertically, the radiale is the point at the most proximal and lateral border of the head of the radius, and the midacromiale-radiale is the point equidistant from the acromiale and radiale landmarks.

It lies within the scope of the disclosure that skinfold thickness at any of the above mentioned skinfold sites or other skinfold sites can be measured to select the at least one donor subject who can donate allogenic fecal matter for use in the treatment according to the present disclosure, wherein the allogenic fecal matter is as defined herein.

The at least one donor subject can be selected by, in addition to having a Body Mass Index (BMI) of at least 30 kg/m$^2$, a HOMA-IR value of at most 2.5 mg/dL and/or an age of at most 60 years, having a thickness of the triceps skinfold site of at most 40 mm, preferably at most 32 mm, such as 20 to 30 mm. A biceps skinfold site can be at most 25 mm, preferably at most 18 mm, such as 9 to 17 mm. A medial calf skinfold site can be at most 39 mm, preferably at most 32 mm, such as 16 to 31 mm. An abdominal skinfold site can be at most 46 mm, preferably at most 38 mm, such as 28 to 37 mm.

According to the disclosure, in addition to having a Body Mass Index (BMI) of at least 30 kg/m2, a HOMA-IR value of at most 2.5 mg/dL, and/or an age of at most 60 years, the at least one donor subject is selected to have a waist circumference to height ratio of preferably between 0.45 and 0.70 m/m, more preferably between 0.50 and 0.65 m/m, even more preferred between 0.55 and 0.65 m/m, and most preferred between 0.58 and 0.62 m/m. The waist circumference is thus the height of the donor subject in meters divided by the waist circumference in meters. Transplantation of fecal matter from donors having such a waist circumference to height ratio may further increase PFS and may further enhance the response of recipients to chemotherapy, reduce toxicity/side effects of chemotherapy, and/or improve quality of life, and/or prolong overall survival of cancer patients.

Waist circumference, also known as the abdominal perimeter, as used herein refers to the measured circumference of the waist at the umbilical level. The umbilical level is the level were the umbilicus, also called the belly button or navel, is located. The waist circumference can be measured with a measuring tape at the position of the belly button, wherein a longitudinal direction of the measuring tape is perpendicular to a longitudinal axis extending from the feet to the head of a subject whose waist circumference is measured.

Alternatively or at the same time, preferably in addition to having a Body Mass Index (BMI) of at least 30 kg/m2, a HOMA-IR value of at most 2.5 mg/dL, and/or an age of at most 60 years, the at least one donor subject may be selected to have a body fat percentage of at most 10, 11, 12, 13, 14, 15, 16, 17, 18, 19, 20, 21, 22, 23, 24, 25, e.g., for male subjects, and/or at most 10, 11, 12, 13, 14, 15, 16, 17, 18, 19, 20, 21, 22, 23, 24, 25, 26, 27, 28, 29, 30 e.g., for female subjects. DEXA/DXA scan is generally considered as an accurate body fat percentage test, but the skilled person is well aware of other suitable methods, such as Bioelectrical impedance analysis (BIA) for determining body fat percentage.

In another aspect of the disclosure a plasma creatine kinase level of the at least one donor subject is preferably at least 500 IU/L, preferably at least 650 IU/L, most preferred at least 800 IU/L. This may result in prolonged overall survival, longer progress-free survival (PFS), better response to chemotherapy, reduced toxicity/side effects of chemotherapy, and/or improved quality of life of cancer and/or cachexia patients.

Creatine kinase is also known as phosphocreatine kinase or creatine phosphokinase (enzyme commission number 2.7.3.2). It catalyzes the reversible reaction of creatine to phosphocreatine. Normal activity values of creatine kinase in blood plasma range between 60 and 400 IU/L.

The use according to the present disclosure may involve determining one or more of BMI value, HOMA-IR value, age, waist circumference, waist circumference to height ratio, body fat percentage, fasting blood insulin level, a fasting blood glucose level, a blood triglyceride level, fasting high-density lipoprotein (HDL) cholesterol level, and blood pressure, a supraspinale skinfold thickness, a subscapular skinfold thickness, and blood pressure for a pool of subjects, and subsequent selection of one or more donor subjects as defined herein, for example, one or more donor subjects having a BMI, HOMA-IR, age, waist circumference, waist circumference to height ratio, body fat percentage, fasting blood insulin level, a fasting blood glucose level, a blood triglyceride level, fasting high-density lipoprotein (HDL) cholesterol level, blood pressure, supraspinale skinfold thickness, and/or subscapular skinfold thickness as defined herein.

The selected donors may, for example, have any of the following relevant features or a combination thereof: a BMI value can range between 30 and 40 kg/m$^2$, such as between 32 and 35 kg/m$^2$; a HOMA-IR value between 0.3 and 2.5 mg/dL, such as between 0.5 and 0.9 mg/dL; an age between 18 and 60 years, such as between 20 and 40 years; a waist circumference between 80 and 120 cm, such as between 95 and 105 cm; waist circumference to height ratio between 0.45 and 0.70 m/m, such as between 0.55-0.65 m/m, a body fat percentage of below 20% for male subjects and below 25% for female subjects; a fasting blood insulin level of at most 25 mIU/L, such as between 3 and 8 mIU/L; a fasting blood glucose level of at most 130 mg/dL, such as between 70 and 100 mg/dL; a blood triglyceride level of at most 150 mg/dL, such as 50-150 mg/dL; a fasting high-density lipoprotein (HDL) cholesterol level of at least 40 mg/dL for men and 50 mg/dL for women, such as 50-90 mg/dL for men and 60-90 mg/dL for women; a supraspinale skinfold thickness of at most 36 mm, such as a thickness between 20 and 30 mm; a subscapular skinfold thickness of at most 40 mm, such as a thickness between 20 and 32 mm; and/or a blood pressure of at most 140/90 mmHg, such as a blood pressure between 90/60 and 120/80 mmHg.

Selected donor subjects can have a BMI between 30 to 40 $kg/m^2$, a HOMA-IR value of 0.5 to 1.5 mg/dL and/or an age below 30 years. The BMI of such donor subjects could range between 30 and 35 $kg/m^2$, such as 32 to 34 $kg/m^2$. A HOMA-IR value of such donor subjects could range between 0.5 and 1.2 mg/dL, such as 0.5 to 0 9 mg/dL. The donor subject could have an age between 18 and 30 years, such as 20 to 25 years.

Preferably a donor subject has a BMI between 32 and 36 $kg/m^2$, a HOMA-IR value between 0.3 and 1.0 mg/dL and an age between 20 and 30 years. A supraspinale skinfold thickness of such a donor could be between 16 and 32 mm, such as 20 to 28 mm. This donor subject can very well have an abdominal perimeter, or waist circumference above 102 cm, but may not have metabolic syndrome.

Preferably a donor subject has a BMI between BMI between 32 and 36 $kg/m^2$, a HOMA-IR value between 0.3 and 2.0 or between 0.3 and 1.0 mg/dL and an age between 20 and 30 years. A waist circumference to height ratio of such a donor could be between 0.54 and 0.64 m/m, such as 0.56 to 0.62 m/m. This donor subject can very well have an abdominal perimeter, or waist circumference above 102 cm, but preferably does not have metabolic syndrome.

The fecal matter according to the present disclosure can be feces, i.e., excreta discharged from the intestine (anus), such as (morning) stool, or part thereof, and/or a composition derived therefrom. The fecal matter may be purified, suspended in medium, filtered, centrifuged, or otherwise processed such as stabilized and freeze-dried to obtain a composition suitable for oral administration or for administration in the gastro-intestinal tract of a receiving subject.

In one aspect of the disclosure, the fecal matter comprises a total of at least 5, 6, 7, 8, 9, 10, 11, or 12 different phyla selected from bacterial phyla and archaeal phyla, preferably at least 16 different phyla, more preferably at least 18 different phyla, most preferred between 20 and 34 different phyla. This may result in further prolonged overall survival, longer progress-free survival (PFS), better response to (chemo) therapy, reduced toxicity/side effects of (chemo) therapy, and/or improved quality of life of cancer and/or cachexia patients.

A total number of phyla can be determined by 16 S rRNA amplicon sequencing as described in Clarke et al, Exercise and associated dietary extremes impact on gut microbial diversity, Gut microbiota, 2014.

The phyla can be selected from a group comprising the bacterial phyla: Acidobacteria, Actinobacteria, Aquificae, Armatimonadetes, B acteroidetes, Caldiserica, Chlamydiae, Chlorobi, Chloroflexi, Chrysiogenetes, Cyanobacteria, Deferribacteres, Deinococcus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia; and/or a group comprising the archaeal phyla: Crenarchaeota, Euryarchaeota, Korarchaeota, Nanoarchaeota, and Thaumarchaeota. Preferably, the fecal matter according to the present disclosure comprise the phyla Bacteroidetes, Firmicutes, Proteobacteria, Actinobacteria and/or Verrucomicrobioa (and Eurachaeyota).

In the context of the present disclosure, the cancer can be any type of cancer, including systemic and localized (organ specific) cancer. The cancer can be bladder cancer, bone cancer, brain cancer, breast cancer, colorectal cancer, endometrial cancer, esophageal cancer, gastric cancer, gastro-esophageal cancer, head and neck cancer, liver cancer, lung cancer, lymphoma, oral cavity cancer, ovarian cancer, pancreatic cancer, prostate cancer, skin cancer, stomach cancer, throat cancer, thyroid cancer, or uterine cervical cancer.

In a particular embodiment of the present disclosure, the cancer is chosen from oesophageal cancer, gastric cancer, gastro-oesophageal junction cancer, and pancreatic cancer. Patients with one of these types of these cancer particularly benefit from allogenic fecal matter as described herein, e.g., obtained from at least one donor subject, wherein the at least one donor subject has a Body Mass Index (BMI) of at least 30 $kg/m^2$; and a HOMA-IR value of at most 2.5 mg/dL and/or an age of at most 60 or at most 40 years.

The average overall survival time of patients with these types of cancer receiving FMT from allogenic donors as described herein may be increased by 25% as compared to patients receiving FMT from autologous donors. In addition, fecal matter obtained from donors having a BMI above 25, such as a BMI above 30, and a HOMA-IR value below 2.5, such as below 1.0, and aged below 40 years, is particularly suited to increase the overall survival time and progression free survival of these types of cancer patients.

Oesophageal cancer, or esophageal cancer occurs in cells of the esophagus, an elongated hollow tube connecting the throat to the stomach. The esophagus moves swallowed food toward the stomach. The formation of tumors in the esophagus caused by esophageal cancer hinders this movement by narrowing of the esophagus tube. Common symptoms of esophageal cancer are difficulty in swallowing, a hoarse throat, and pain in the region around the stomach. Esophageal cancer can be classified in two main types: esophageal squamous-cell carcinoma (ESCC) and esophageal adenocarcinoma (EAC). Risk factors for ESCC include smoking, drinking alcohol, and a poor diet. For EAC risk factors include smoking, acid reflux, and obesity.

The prognosis of esophageal cancer is poor, as only 13-18% of patients are still alive 5 years after diagnosis. An important reason is the relatively late diagnosis, as symptoms often do not occur before the esophageal cancer is in an advanced stage.

Gastric cancer, also known as stomach cancer occurs in cells of the stomach. The stomach is a hollow digestive organ located between the esophagus and the duodenum. Gastric acid and various enzymes are secreted by the stomach to aid in the digestion of food. Common symptoms of gastric cancer are loss of appetite, nausea and vomiting, acid indigestion, melena, and weight loss. Risk factors for gastric cancer are *Helicobacter pylori* infection, smoking, a poor diet, and obesity. The prognosis of stomach cancer is also quite poor. About 32% of patients are still alive 5 years after diagnosis. As with esophageal cancer, symptoms most often occur when the cancer has reached an advanced stage, resulting in the poor prognosis.

Gastro-esophageal junction cancer occurs in glandular cells located near the gastro-esophageal junction, the lower part of the esophagus that connects with the stomach. Common symptoms of gastro-esophageal cancer include pain when swallowing, weight loss and nausea and vomiting. Gastro-esophageal cancer is considered to be a form of esophageal cancer and is treated similarly. Risk factors include obesity, smoking, drinking alcohol, and a poor diet. Similar to esophageal cancer and stomach cancer, the five-year survival rate for gastro-esophageal cancer heavily depends on the stage of the cancer when its diagnosed and ranges between 5-43%.

Pancreatic cancer occurs in cells of the pancreas, an organ of the digestive system located near the stomach, which regulates blood sugar levels and neutralizes acid entering the duodenum. The most common form of pancreatic cancer is pancreatic adenocarcinoma. Common symptoms of pancreatic cancer include loss of appetite, weight loss, yellowing of the skin, and back pain. Risk factors include smoking, diabetes, and obesity. The prognosis of pancreatic cancer is very poor, as the average five-year survival rate is only 6%.

According to the disclosure, the cancer may be metastatic cancer. Metastatic cancer is cancer that has spread locally by moving to nearby tissue from its place of origin. For many types of cancer, metastatic cancer is referred to as stage IV cancer. The process of spreading of the cancer is called metastasis. Metastatic cancer is more difficult to treat compared to localized cancer. Palliative care is applied more often in metastatic cancer. It is found that FMT in the case of metastatic cancer, allogenic FMT greatly increases the quality of life (QoL).

A cancer type of the cancer may be chosen from adenocarcinoma, squamous cell carcinoma, and undifferentiated carcinoma. An adenocarcinoma (AC) can develop at various locations in the body. It is a type of excessive and abnormal growth of epithelial cells, which synthesize substances for release elsewhere in the body (glandular cells). Adenocarcinomas are a common form of esophageal cancer, pancreatic cancer, stomach cancer and gastro-esophageal cancer.

Squamous cell carcinoma originates in squamous cells. These cells appear as polygonal plates when viewed from the top. These cells are located near the surface of tissues within body cavities, allowing diffusion of compounds through these cells (surface lining cells). Squamous cell carcinomas are a common form of esophageal cancer A carcinoma is undifferentiated when it does not resemble any normal glandular cells or surface lining cells. Undifferentiated carcinomas have a very poor prognosis, as the clinical course is more aggressive than differentiated carcinomas such as adenocarcinoma and squamous cell carcinoma.

In a further aspect of the disclosure, the cancer is accompanied by cachexia and/or sarcopenia. The disclosure reduces the detrimental effects of cachexia on the body and leads to prolonged overall survival, longer progress-free survival (PFS), better response to chemotherapy, reduced toxicity/side effects of chemotherapy, and/or improved quality of life.

Cachexia can be described as a condition of irreversible wasting, i.e., progressive weakening and emaciation, of the body, which may be associated with cancer. Age-associated physiologic muscle wasting and weakness is known as sarcopenia. Sarcopenia can occur in older adults in combination with cachexia. In cachexia skeletal muscle and adipose tissue is used for nutrition of the body, lowering the ability of cancer patients to withstand cancer treatment by chemotherapy and radiotherapy. In general, cancer patients with cachexia die when their weight loss exceeds 25 to 30%.

The disclosure also relates to the use of the allogenic fecal matter as described herein for the treatment of cachexia, sarcopenia and/or anorexia nervosa, e.g., wherein the allogenic fecal matter is obtained from at least one donor subject, wherein the at least one donor subject is as defined herein and has, for example, a Body Mass Index (BMI) of at least 30 kg/m$^2$;

a HOMA-IR value of at most 2.5 mg/dL and/or an age of at most 60 years.

Congestive heart failure, chronic obstructive pulmonary disease, chronic kidney disease and AIDS can also be accompanied by cachexia and/or sarcopenia, and are thus encompassed by the present disclosure. Also anorexia nervosa is encompassed by the present disclosure and can be characterized by low weight, food restriction, fear of gaining weight, and a strong desire to be thin. The diagnostic criteria (DSMS) include restriction of energy intake relative to requirements leading to a low body weight, intense fear of gaining weight or persistent behaviors that interfere with gaining weight, and disturbance in the way a person's weight or body shape is experienced or a lack of recognition about the risks of the low body weight.

The allogenic fecal matter according to the present disclosure may be administered to the small intestine, preferably the duodenum, of the subject. Administration to the duodenum is beneficial, as the fecal matter is not influenced by other parts of the gastro-intestinal tract upstream of the duodenum, such as the stomach. The duodenum is the first section of the small intestine, preceding the jejunum and ileum and is the shortest part of the small intestine. In humans, the duodenum is a hollow tube of 25-38 cm, which connects the stomach to the distal duodenum. It begins with the duodenal bulb and ends at the suspensory muscle of duodenum.

Preferably, the allogenic fecal matter for use according to the present disclosure is feces or part thereof, preferably a purified part thereof. By purifying the fecal matter, the fecal matter can be more conveniently introduced in the duodenum of the receiving subject. As there is less debris in the purified fecal matter, its flow rate through a probe used to administer the fecal matter is enhanced, reducing the thickness of the probe, and as such, reducing the discomfort for the receiving subject.

A part of fecal matter as used herein denotes one or more specific groups of components including, but not limited to: enzymes, proteins, lipids, molecules, microorganisms, viruses, bacteria, fungi, yeast, archaea, compounds, complexes, solids, liquids, particles, and fibers.

A purified part of fecal matter as used herein denotes that undesired groups of components are not present in the fecal matter.

Preferably, the allogenic fecal matter for use according to the disclosure is comprised in liquid medium and/or does not comprise solids having a diameter of more than 10, 25, 50, 75, 100, 200, 400, 600, 800, or 1000 μm, preferably obtained by mixing allogenic feces with aqueous medium and subsequent filtering and/or centrifugation. This greatly reduces the viscosity and enhances flow of the fecal matter, facilitating administration of the fecal matter in the gastro-intestinal tract, or duodenum of the receiving subject. The liquid medium can comprise water, or another type of liquid that may be supplemented with other components, such as salts, to provide an isotonic solution.

Preferably, the allogenic fecal matter for use according to the disclosure is combined with a chemotherapeutic agent, preferably chosen from the group consisting of capecitabine or oxaliplatin. This combination with a chemotherapeutic agent can be very effective in the treatment of cancer as it prolongs overall survival, cumulative survival, enhances PFS and reduces side effects of cancer and cancer treatment.

Capecitabine is a chemotherapeutic agent used to treat various cancer types such as esophageal cancer, stomach cancer, and breast cancer. It is converted to 5-fluorouracil in the body, which is a thymidylate synthase inhibitor. Thymidylate synthase is required for de novo DNA synthesis. As cell division requires DNA synthesis, capectiabine inhibits the formation of cancer cells.

Oxaliplatin is a chemotherapeutic agent containing a platinum atom that can be used together with capecitabine. Oxaliplatin is cytotoxic and forms crosslinks in DNA, preventing its replication and transcription, resulting in cell death. Oxaliplatin is often used to treat colorectal cancer.

According to one aspect of the disclosure, the fecal matter according to the disclosure is comprised in a composition, preferably a pharmaceutical composition, more preferably a liquid or solid dosage form, most preferably a capsule, a tablet, or a powder, facilitating administration of the fecal matter to a recipient.

It is further envisaged that the fecal matter according to the present disclosure is present in lyophilized and/or micro-encapsulated form. These forms enable the preservation of the fecal matter, allowing storage thereof for longer periods of time, such as several months or years.

The use according to the disclosure preferably involves at least 1, 2, 3, 4, 5, 6, 7, 8, 9, 10 separate administrations of fecal matter obtained from the at least one donor subject to e.g., the small intestine, preferably the duodenum, of the recipient, preferably with intervals of at least 1, 2, 3, 4, 5, 6, 7, 8 weeks between the separate administrations.

According to the present disclosure, the fecal matter may be administered by enteral, preferably by oral, nasal or rectal administration, and/or by nasoduodenal tube administration.

For oral administration, the fecal matter, e.g., one or more constituents of autologous feces, preferably a lyophilized form thereof (see e.g., Tian H, et al. J Clin Gastroenterol. 2015; or Hecker M T, et al. Open Forum Infect Dis. 2016), may be administered in solid dosage forms, such as capsules, tablets, and powders, or in liquid dosage forms, such as elixirs, syrups, and suspensions. Also a carrier can be applied, such as activated carbon.

The fecal matter may be used as medicament and/or accompanied by a physiologically acceptable carrier, which may be any inert carrier. For instance, non-limiting examples of suitable physiologically or pharmaceutically acceptable carriers include any well-known physiological or pharmaceutical carriers, buffers, diluents, and excipients. It will be appreciated that the choice for a suitable physiological carrier will depend upon the intended mode of administration of the composition as taught herein (e.g., oral) and the intended form of the composition (e.g., beverage, yogurt, powder, capsules, and the like). The skilled person knows how to select a physiologically acceptable carrier, which is suitable for or compatible with the compositions for use as taught herein.

It is envisaged that the fecal matter is comprised in and/or encapsulated by an (enteric) coating, preferable wherein the coating does not dissolute and/or disintegrate in the gastric environment of the subject. Such coating may help the fecal matter to reach the intended site for delivery, e.g., the duodenum, without suffering breakdown due to the acidic environment of the stomach. Preferred (enteric) coatings work by presenting a surface that is stable at the highly acidic pH found in the stomach, but breaking down more rapidly at a lower pH. For example, it will not dissolve in the gastric acids of the stomach (pH ~3), but it will dissolve in the alkaline (pH 7-9) environment present in the small intestine, or duodenum.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

Example 1

A randomized double-blinded placebo controlled interventional trial was designed. It was aimed to include 16 patients with metastasized or locally advanced oesophageal or gastric cancer receiving standard first-line palliative chemotherapy. This treatment involves 3 weekly cycles of capacitabine (1000 mg/m$^2$, 2 times a day from day 1 to 14) and oxaliplatin (130 mg/m$^2$ on day 1) with a maximum of 6 consecutive cycles, followed by capecitabine maintenance therapy (Table 1).

TABLE 1

Chemotherapy regime in patients with metastasized or locally advanced oesophageal or gastric cancer: CAPOX-treatment.

| Medicine | Week 1 (Day 1) | Week 1-2 (Day 2-14) | Week 3 (Day 15-21) |
|---|---|---|---|
| Oxaliplatin | * | REST | REST |
| Capecitabine | * | * | REST |

Screening and Inclusion

A screening visit was performed in the AMC (Academisch Medisch Centrum, Amsterdam). During this screening in- and exclusion criteria were verified and, after oral and written explanation of the study, informed consent was obtained. Medical history was recorded and physical examination took place including body weight, height, waist and hip circumference and blood pressure. If participants were found to be eligible for the study they were randomized to the following 2 treatment arms:

1. Autologous fecal transplantation (n=12)
2. Allogenic fecal transplantation from obese subjects (n=12)

Study Visits and Measurements

There were 2 extra study visits at baseline and after 4 weeks (visit at 12 weeks was combined with regular outpatient clinic visit). Before every visit, subjects had fasted overnight. A total amount of blood obtained during this study was 180 ml: 60 ml at 0, 4 and 12 weeks (the latter taken in combination with regular blood during regular treatment follow-up in the outpatient clinic). Since it is standard procedure to perform a CT-scan to evaluate the treatment response, no additional imaging to measure muscle mass (sarcopenia) was needed for this study.

Study Visits Patients: Baseline, 4 and 12 Weeks

Before both visits, subjects collected feces samples of 48 hours, a sample of morning stool and 24 hours urine. First a resting energy expenditure (REE) and Bio Impendence Analysis (BIA) was assessed. In addition, subjects were weighed to determine their BMI and blood was drawn (60 ml per visit). Questionnaires for levels of hunger were filled out, as well as evaluation of chemotherapy toxicity, graded with the Common Terminology Criteria for Adverse Events (CTCAE). At baseline, fecal transplantation was performed by placement of duodenal tube (using coretrack). After placement of the duodenal tube faecal transfusion was performed (autologous or allogenic according to the randomization). The day before the fecal transplantation, bowel lavage was performed, by drinking 1 liter Macrogol after dinner (between 7 p.m. and midnight).

Study Visit Donors: Baseline

At baseline, donors collected feces samples of 48 hours, a sample of morning stool (for transplantation) and 24 hours-urine. First a resting energy expenditure (REE) and a Bio Impendence Analysis (BIA) were assessed. Questionnaires for levels of hunger were filled out. Fresh morning feces was used for each donation.

Subject Inclusion Criteria

In order to be eligible to participate in this study, patients must meet all of the following criteria:

- Male or female with metastasized or locally advanced oesophageal and/or gastric cancer receiving standard first-line palliative chemotherapy (capecitabine/oxaliplatin)
- Age between 30-70 years
- Meeting the criteria for sarcopenia, using computed tomography (CT)-scan: the L3 muscle area surfaces will be normalized for patient height to calculate the L3 muscle index and expressed in $cm^2/m^2$. The cutoff values used for sarcopenia are 52.4 $cm^2/m^2$ for men and 38.5 $cm^2/m^2$ for women, based on the method of Prado et al[2]
- Meeting the International Classification of Functioning, Disability and Health (ICF)[3], WHO 1, 2 or 3.
- Stable medication use, all subjects use PPI.
- Subjects should be able and willing to give informed consent Subject Exclusion Criteria A potential subject who meets any of the following criteria will be excluded from participation

- In this Study:
  - Smoking, XTC, amphetamine or cocaine abuse
  - Alcohol abuse (>3/day)
  - Cholecystectomy
  - HIV infection with a CD4 count <240
  - Chronic nausea, altered taste sensation, swallowing difficulties or mechanical obstruction due to the malignancy.
  - History of neurological disease or psychiatric disorder.
  - Patients with diabetes mellitus (there are several studies indicating that a high level of NLR may reflect ongoing vascular inflammation and play an important role in the pathophysiology of DM and even prediabetes)[4].

Subject Screening

Starting with 46 subjects, 3 had diabetes mellitus, 1 received antibiotics, 2 did not undergo CAPOX treatment and 2 were excluded for not meeting the International Classification of Functioning, Disability and Health (ICF)[3]. Of the remaining 38 subjects, 10 subjects were excluded because the study was too stressful or burdensome for them and another 4 subjects were excluded because of extensive travel time. The remaining 24 patients underwent randomization into 2 groups. 12 patients were placed in an autologous transplantation group, and the remaining 12 patients were placed in an allogenic transplantation group. Table 2 below shows characteristics of these patients in both groups (Autologous (n=12) and Allogenic (n=12)). Wherein n denotes the number of subjects, square brackets contain the lowest and highest values (age or BMI), and percentages between brackets indicate the number of subjects in a specific class (male or female) divided by the total number subjects within one of the groups (autologous or allogenic), expressed as a percentage.

TABLE 2

| Data participating subjects | Autologous (n = 12) | Allogenic (n = 12) |
|---|---|---|
| Age (years) | 62.6 [53.5-69.75] | 63.0 [58.8-70.3] |
| BMI (kg/m²) | 25.7 [21.08-31.62] | 23.6 [19.6-29.07] |
| Sex (n) | | |
| Male | 8 (66.7%) | 11 (91.7%) |
| Female | 4 (33.3%) | 1 (8.3%) |
| Subsite of tumor (n) | | |
| Esophagus | 10 | 9 |
| Gastroesophageal junction | 1 | 1 |
| Stomach | 1 | 2 |
| Performance-status score (n) | | |
| 0 or 1 | 9 | 10 |
| 2 | 3 | 2 |
| Type of tumor (n) | | |
| Adenocarcinoma | 10 | 11 |
| Squamous-cell carcinoma | 2 | 1 |
| Number of metastatic sites (n) | | |
| 0 or 1 | 6 | 4 |
| ≥2 | 6 | 8 |
| Previous surgery (n) | 5 | 3 |

Of the 24 selected subjects, 8 were excluded during the study. Of these 8 subjects, 3 received antibiotics during the study, 3 subjects deceased, and 4 subjects withdrew from the study. In the end, 16 subjects finished the study.

Donor Inclusion Criteria

In order to be eligible to participate as a feces donor in this study, a subject must meet all of the following criteria:

- Caucasian male or female
- 18-70 years old
- BMI >30 $kg/m^2$

Donor Exclusion Criteria

A potential donor who meets any of the following criteria will be excluded from participating as donor in this study:

- Presence of chronic low-grade inflammation or criteria of metabolic syndrome
- Use of any medication including PPI and antibiotics
- Presence of type 2 diabetes or hypertension
- Diarrhea
- Cholecystectomy
- HIV, HAV, HBV, HCV, active CMV, active EBV, IBD
- Unsafe Sex Practice (Questionnaire)
- Presence of fecal bacterial pathogens (*Salmonella, Shigella, Campylobacter, Yersinia*) or parasites
- Positive *C. difficile* stool test
- Individuals with an increased risk for one of the above conditions (homosexual contacts, recent blood transfusions) will be excluded, and donors are not recruited amongst health care providers.

Sample Size Calculation

Sample size calculation was based on the Visual Analog Scale (VAS) results for satiety (primary endpoint) and appetite (secondary endpoint). Based on an expected mean 15 mm (SD 10 mm) increase in VAS score upon an allogenic lean donor FMT versus 5 mm increase upon autologous FMT. Taking two-sided p value (alpha) of 0.05 and 80% power, 16 subjects in total were needed. Ideally, cancer patients will be allocated to a single healthy obese donor and therefore a maximum of 8 donors are needed for feces donation. An interim analysis after these 16 patients was done to redo the power calculation.

Main Study Parameter/Endpoint

Satiety, measured by the Visual Analog Scale (VAS) questionnaire

Body composition measured by Bio Impedance Analysis (BIA)

Treatment response measured by CT-scan at baseline and after the first 3 cycles of chemotherapy (week 12).

Overall survival (defined as the number of days of survival after PA diagnosis).

Randomization, Blinding and Treatment Allocation

Patients were randomized by computer program (ALEA). Blinding was guaranteed by combined fecal transplantation in both groups. On the day of fecal transplantation both subject and donor will deliver morning feces. Randomization and preparation of the feces was performed by one of the research assistants. He/she is the only person who knows which treatment the subject has received and has no further part in the study. Feces was put in a 500 ml glass bottle and looks like a brownish fluid not recognizable as feces from the donor or subject and given to the investigator who performed nasoduodenal tube infusion. Subject, donor and investigator were all blinded. Ample experience with this procedure (>300 fecal transplants at the AMC in the last 8 years) has been obtained.

Screening of Feces Donors

Potential donors will be thoroughly screened according to the protocol used in the FAECAL & FATLOSE trial as previously approved by the METC (MEC 07/114 and 11/023). Donor feces was collected from obese donors, who were screened according to the guidelines of the Dutch Blood Bank Association (section: Donor exclusion criteria). Donors underwent an indirect calorimetry (resting energy expenditure) and Bio Impedance Analysis (BIA), as well as blood sampling (60 ml).

Preparation Fecal Clysma for Fecal Transplantation

Donor and recipient delivered a fresh feces sample (150-250 grams on average) on the day of infusion (produced within 24 hours before use). After collection in a plastic flask, feces was covered by saline and stored at room temperature. Time of collection was written down. All procedures were performed at the department of Clinical Bacteriology, AMC. All steps were performed in a fumehood by an experienced lab co-worker or the investigator. Fresh feces solution was mixed during 10 minutes until fully homogenized. Hereafter, the faeces solution was poured through a clean metal sieve and food derived debris of large size was removed. This step was repeated. Hereafter, the homogenized solution was decanted through a clean metal funnel into a 1000 ml sterile glass bottle. Thereafter, a sample of the processed fecal infusate was taken for later analysis and the bottle was kept on normal room temperature (17° C.) until the patient was finished with bowel lavage.

Bowel Lavage

Bowel was lavaged with 3-4 liter of Macrogol (Klean Prep), depending on the subjects weight (>60 kg 4 liter, <60 kg 3 liter) the evening before the fecal transplantation (according to standard protocols) to ensure complete bowel lavage (duration 3-4 hours).

Fecal Infusion

Finally, the filtered and mixed fecal transplant (<6 hours after processing) was infused in the duodenum through a duodenal tube.

Resting Energy Expenditure (REE)

REE was measured at baseline and after 4 weeks by indirect calorimetry. Oxygen consumption and $CO_2$ production were measured during 20 minutes using a ventilated hood system. With these measurements the REE and respiratory quotient (RQ) were calculated. The RQ represents the ratio of carbon dioxide exhaled to the amount of oxygen consumed by the individual and represents whole body substrate oxidation (glucose, fat and protein oxidation). The abbreviated Weir equation was used to extrapolate the 24-hour energy expenditure.

No significant difference in REE of subjects between the allogenic and the autologous group could be observed over the course of 12 weeks (FIG. 1). In addition, no significant difference in REE of subjects over time within each group could be observed. FMT thus appears to not have an effect on the REE of subjects undergoing FMT.

Bio Impedance Analysis (BIA)

Body composition was measured using BIA at baseline and after 4 and 12 weeks. BIA determines the electrical impedance of an electric current through body tissues, which can then be used to calculate and estimate body fat. BIA is a safe, non-invasive and inexpensive bedside method to assess body composition[5].

Figure 2:
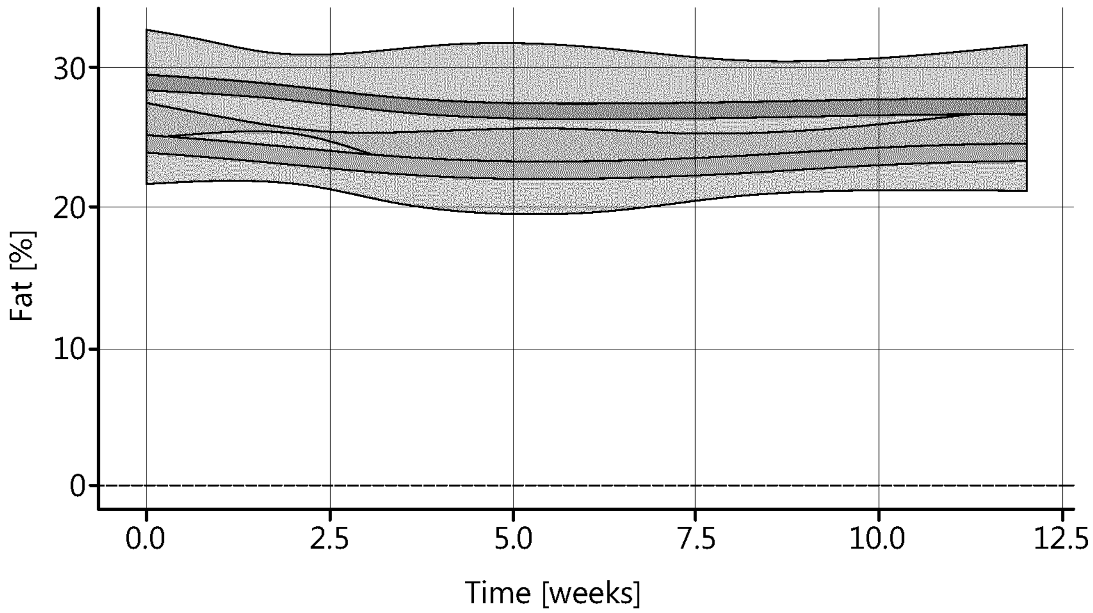
FIG. 2: Mean body fat percentages (measured with Bio Impedance Analysis, BIA) of all subjects receiving allogenic FMT (line with lowest fat percentage at time 0) and of all subjects receiving autologous FMT (line with highest fat percentage at time 0). The shaded areas indicate standard deviations of the mean.

No significant difference in fat percentage of subjects between the allogenic and the autologous groups could be observed over the course of 12 weeks (FIG. 2). In addition, no significant difference in fat percentage of subjects over time within each group could be observed. FMT thus appears to not have an effect on the fat percentage of subjects undergoing FMT.

Assessment of Appetite (VAS Questionnaire)

Figure 3:
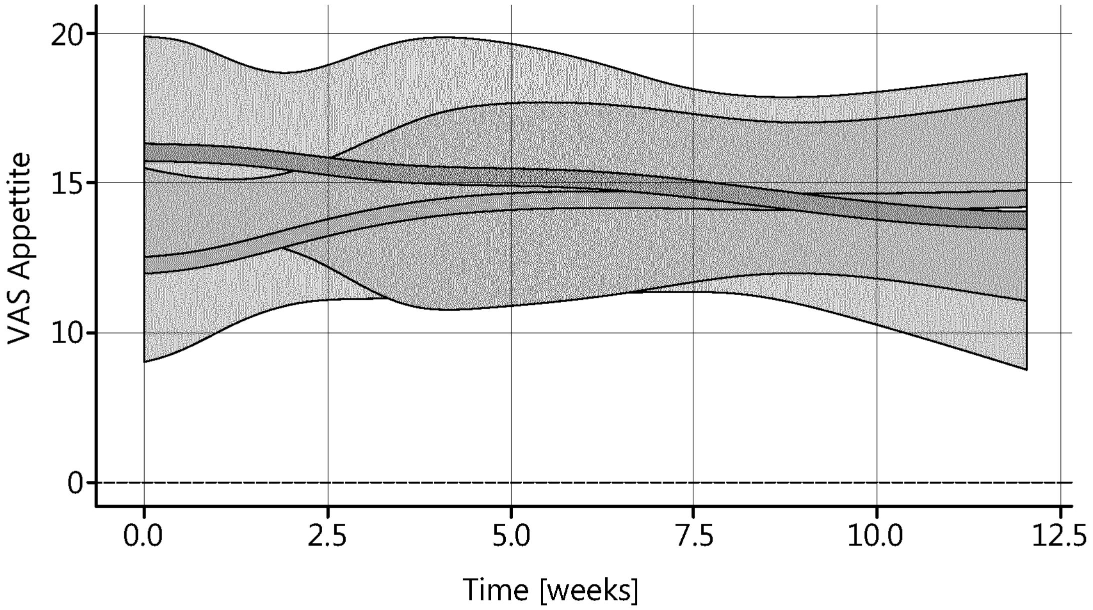
FIG. 3: Mean appetite (measured with the Visual Analog Scale, VAS, questionnaire) of all subjects receiving allogenic FMT (line with lowest VAS score at time 0) and of all subjects receiving autologous FMT (line with highest VAS score at time 0). The shaded areas indicate standard deviations of the mean.

At baseline and 4 and 12 weeks after transplantation, subjects were (next to satiety VAS) also asked to fill out the following questionnaire to measure the level of appetite: Visual analogue scale (VAS): Measuring the level of appetite There appeared to be no effect of FMT on appetite, measured with the Visual Analogue Scale (FIG. 3). No significant difference in appetite of subjects between the allogenic and the autologous groups could be observed over the course of 12 weeks (FIG. 3). In addition, no significant difference in appetite of subjects over time within each group could be observed. FMT thus appears to not have an effect on appetite of subjects undergoing FMT.

Subject BMI Measurements

Figure 4:
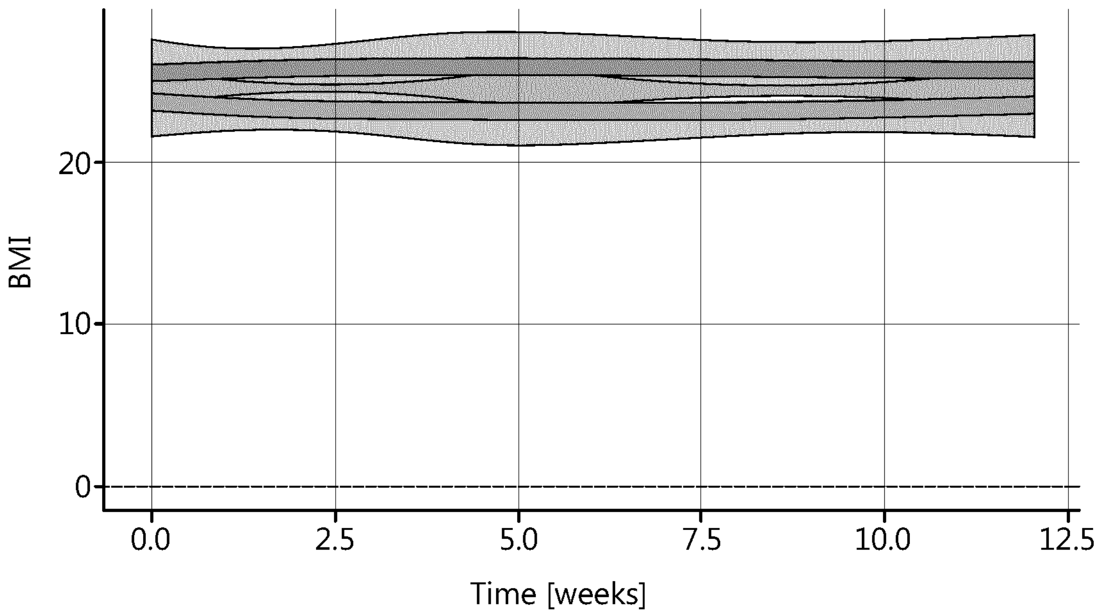
FIG. 4: Mean Body Mass Index (BMI) of all subjects receiving allogenic FMT (line with lowest BMI at time 0) and of all subjects receiving autologous FMT (line with highest BMI at time 0). The shaded areas indicate standard deviations of the mean.

BMI of subjects was measured at the start of the trial (Baseline) and at 4 weeks and 12 weeks. There was no significant change of subject BMI over time observed in both groups (Allogenic and Autologous), as can be observed in FIG. 4.

Treatment Response Measured by CT-Scan

Figure 5:
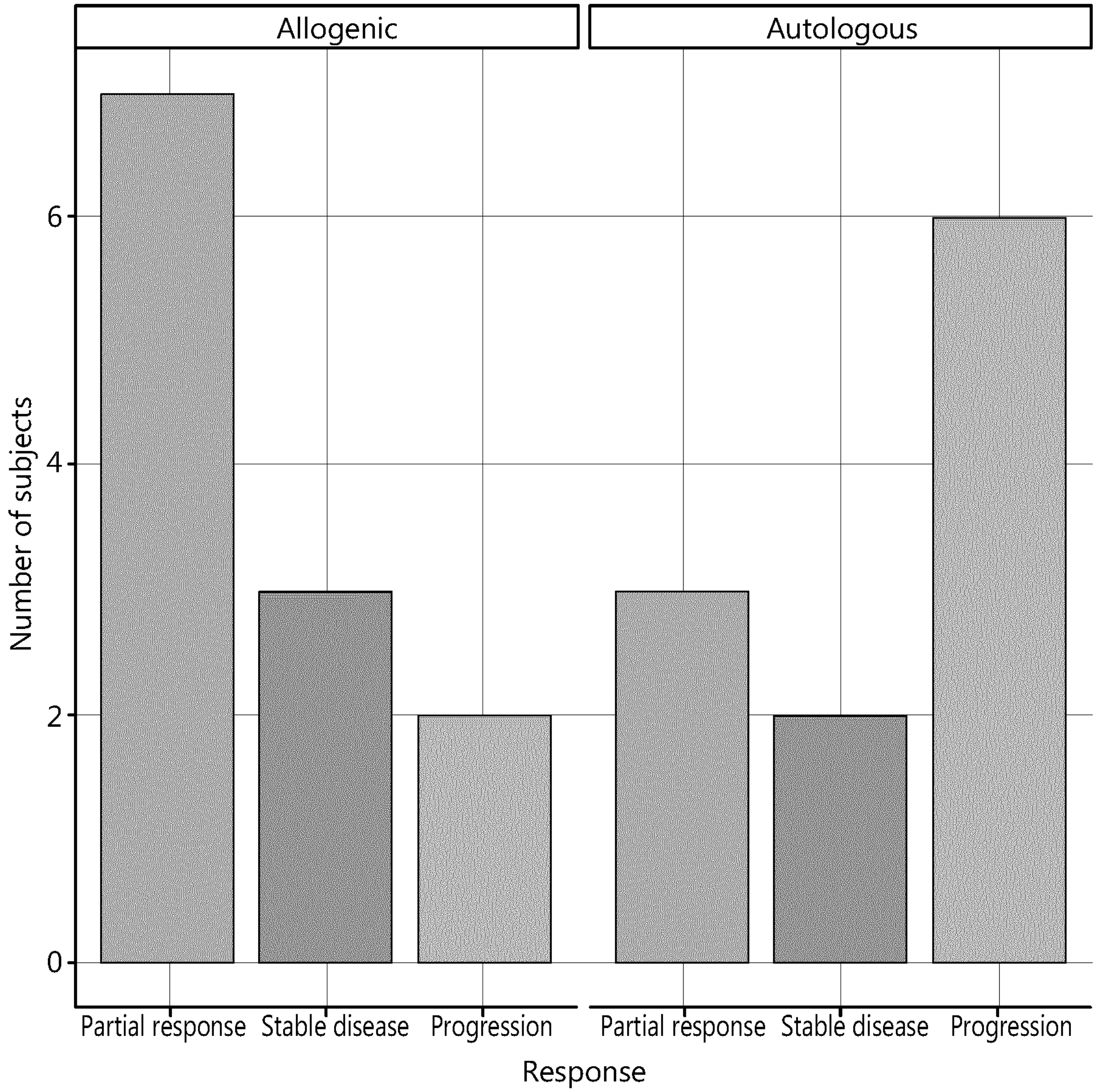
FIG. 5: Response of subjects receiving allogenic FMT (left three bars) and of subjects receiving autologous FMT (right three bars). Each subject was classified in one of three categories: Partial response, Stable disease, and Progression.

The response of subject on the FMT was measured by CT-scan at baseline and after the first 3 cycles of chemotherapy (week 12). The response was classified using Response Evaluation Criteria in Solid Tumors (RECIST) into partial response, stable disease, and progression. Progression is markedly higher in the group undergoing autologous FMT and the partial response is lowered in this group in comparison to the group undergoing allogenic FMT (FIG. 5).

Progression-Free Survival

Figure 6:
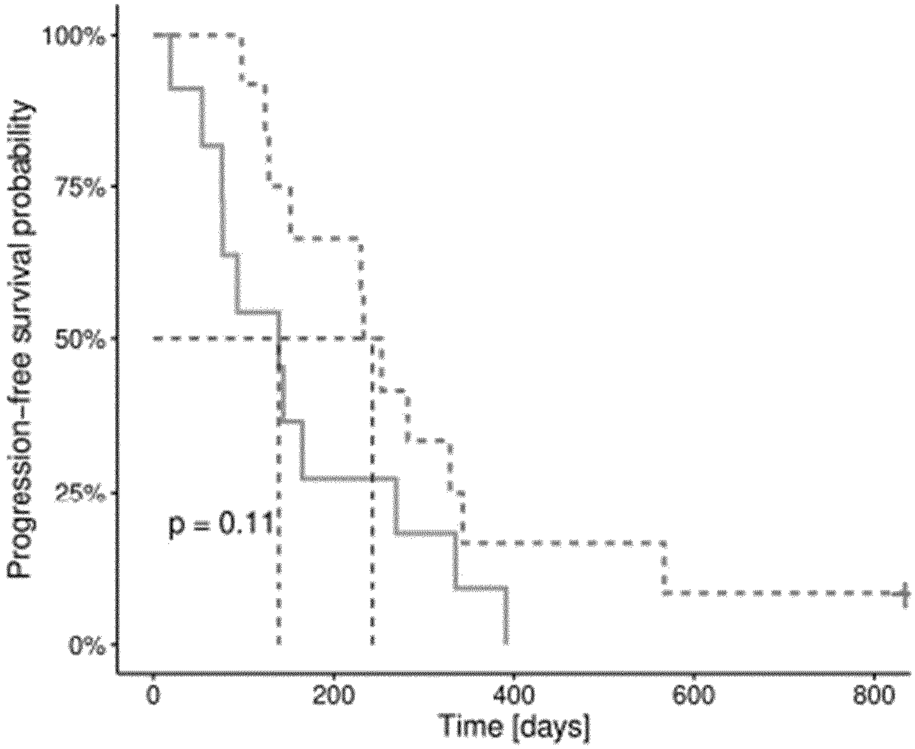
FIG. 6: Progression-free survival probability over time of subjects receiving allogenic FMT (dashed line) and of subjects receiving autologous FMT (solid line).

The median progression-free survival time of subjects from the autologous FMT group was 139 days, while the median progression-free survival time of subjects from the allogenic FMT group was 243 days (FIG. 6). The difference of 104 days (p=0.11) indicates that allogenic FMT has a profound effect on progression-free survival time. Table 3 below shows times of progression-free survival (PFS) and the corresponding percentages of subjects in both groups.

TABLE 3

| Progression-free survival percentages | | |
|---|---|---|
| | Autologous | Allogenic |
| 3 months | 63.3% | 85% |
| 6 months | 27.3% | 66.7% |
| 1 year | 9.0% | 16.7% |

The Cox regression was used to investigate the difference in the hazard of cancer progression between subjects receiving autologous and allogenic FMT. A Cox hazard ratio of 0.497 (P=0.13) was obtained, indicating that subjects in the allogenic group have a 49.7% lower hazard of cancer progression compared to subjects in the autologous group.

Overall Survival

Figure 7:
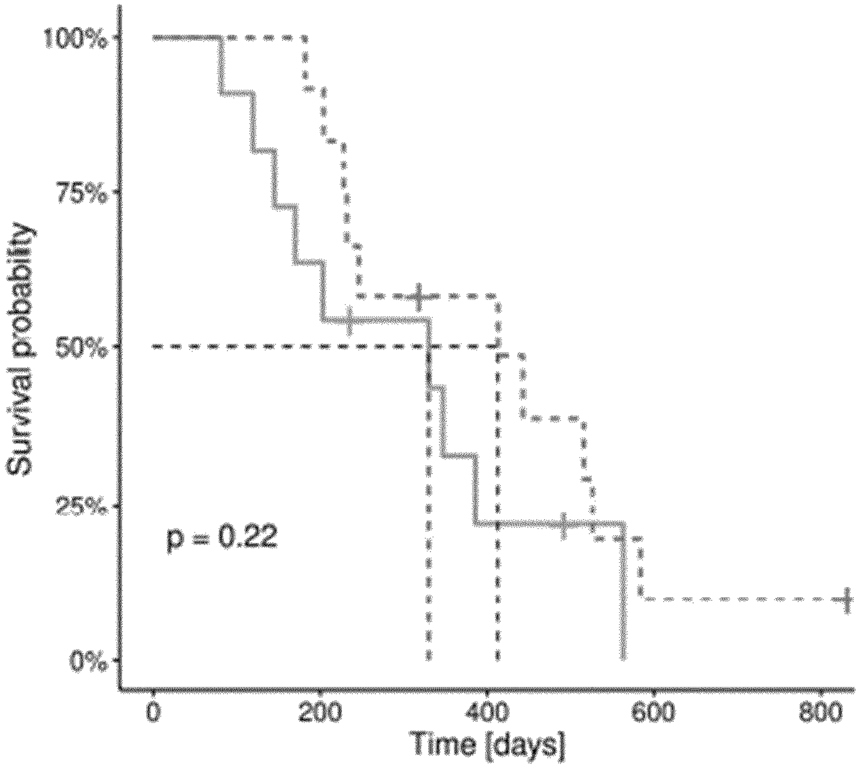
FIG. 7: Survival probability over time of subjects receiving allogenic FMT (dotted line starting at 100%) and of subjects receiving autologous FMT (dashed line starting at 100%).

The median survival time of subjects from the autologous FMT group was 331 days and the median survival time of subjects from the allogenic FMT group was 414 days (FIG. 7). The median survival time for subjects in the allogenic group is thus increased by 83 days (Log-rank test P=0.22). The survival probability at 6 months for the autologous group is 36.6% as compared to 91.6% for subjects in the allogenic group. The survival probability at 1 year (still ongoing) is 32.7% for subjects in the autologous group compared to 58.3% for subjects in the allogenic group.

The Cox Hazard Ratio is 0.561, indicating that subjects receiving allogenic FMT have a 56.1% lower hazard of death compared to subjects receiving autologous FMT.

Quality of Life

Survival times of esophageal cancer are quite poor and most people die within the first year of diagnosis. Therefore, an increase of 104 days of progression free survival of subjects receiving allogenic fecal matter transplantation (FMT) as compared to subjects receiving autologous FMT is a very pronounced effect. The same holds for the increase of 83 days in median survival time in favor of allogenic FMT. Unexpectedly, the appetite of subjects receiving fecal matter from obese donors did not increase (FIG. 3).

In addition to increased survival, quality of life of subjects receiving allogenic FMT is markedly improved. A main objective of palliative care is optimization of quality of life. This objective is, in particular, achieved by the current disclosure as the symptoms of cachexia are decreased in subjects receiving allogenic FMT.

Example 2

Allogenic Fecal Matter Transplantation (FMT) was most effective when fecal matter donors have a BMI of at least 30. However, there appear to be differences in effectiveness of the FMT between donors within this allogenic group. This effect was further studied.

FMT Donors

Within the group of patients receiving allogenic FMT there were 4 different donors (donor 14, 21, 22 and 23). Several characteristics of these donors are listed in Table 4.

TABLE 4

Donors for allogenic FMT and their characteristics

| Study ID (D–) | Age | Sex | Length (m) | Weight (kg) | BMI | Glucose (mmol/l) | Triglicerides (mmol/l) | HDL (mmol/l) | Insuline (pmol/l) | HOMA-IR | Donations |
|---|---|---|---|---|---|---|---|---|---|---|---|
| 14 | 66 | M | 1.86 | 108.5 | 31.4 | 5.1 | 1.2 | 1.49 | 38 | 1.2 | 1 |
| 21 | 67 | M | 1.83 | 104.4 | 31.2 | 5.2 | 1.19 | 1.42 | 86 | 2.9 | 1 |
| 22 | 24 | F | 1.70 | 75.5 | 26.1 | 3.8 | 0.62 | 1.38 | 34 | 0.8 | 4 |
| 23 | 21 | M | 1.78 | 103 | 32.5 | 4.5 | 1.19 | 1.83 | 18 | 0.5 | 6 |

The donations listed in Table 4 indicate the number of patients in the allogenic FMT group receiving FMT from the indicated donor. For example, 4 patients received FMT from donor 22. The response of patients in the allogenic group on FMT from above donors is given in Table 5.

TABLE 5

| Response of patients on FMT | | | |
|---|---|---|---|
| | Donor | Progression | Stable disease or partial response |
| Allogenic | Total | 2 | 10 |
| | 14 | 1 | 3 |
| | 21 | 0 | 1 |
| | 22 | 1 | 0 |
| | 23 | 0 | 6 |
| Autologous | Total | 7 | 5 |

Out of 12 patients in the autologous FMT group, 7 showed disease progression, whereas 5 showed a stable disease or partial response. In contrast, only 2 out of 12 patients in the allogenic FMT group showed disease progression, while the vast majority of 10 patients showed a stable disease or partial response.

Cumulative Survival

The cumulative survival is the proportion of patients surviving past a given time interval. The cumulative survival of patients in both groups (the autologous FMT group and the allogenic FMT group), after one year is given in FIG. 8.

Figure 8:
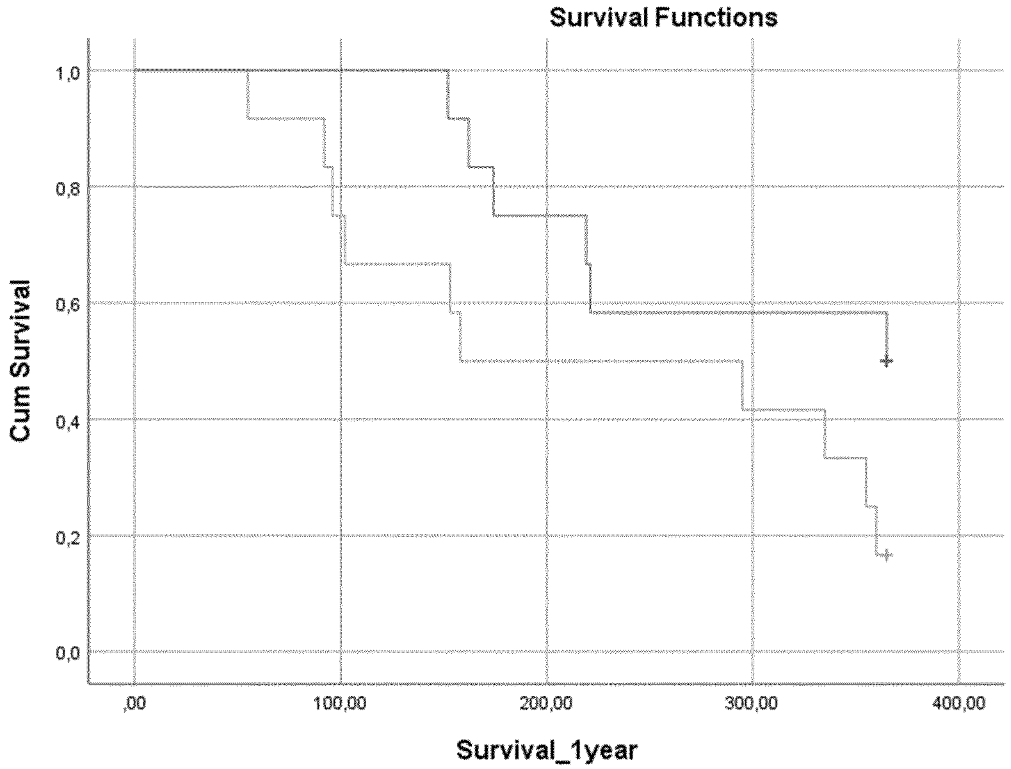
FIG. 8: Cumulative survival over a one year time interval of subjects receiving allogenic FMT (bold line having the highest endpoint, indicated by a "+" sign, after one year) and of subjects receiving autologous FMT (not in bold line having the lowest endpoint, indicated by a "+" sign, after one year).

As can be seen in FIG. 8, patients receiving allogenic FMT have a higher cumulative survival after one year as compared to patients receiving autologous FMT.

Figure 9:
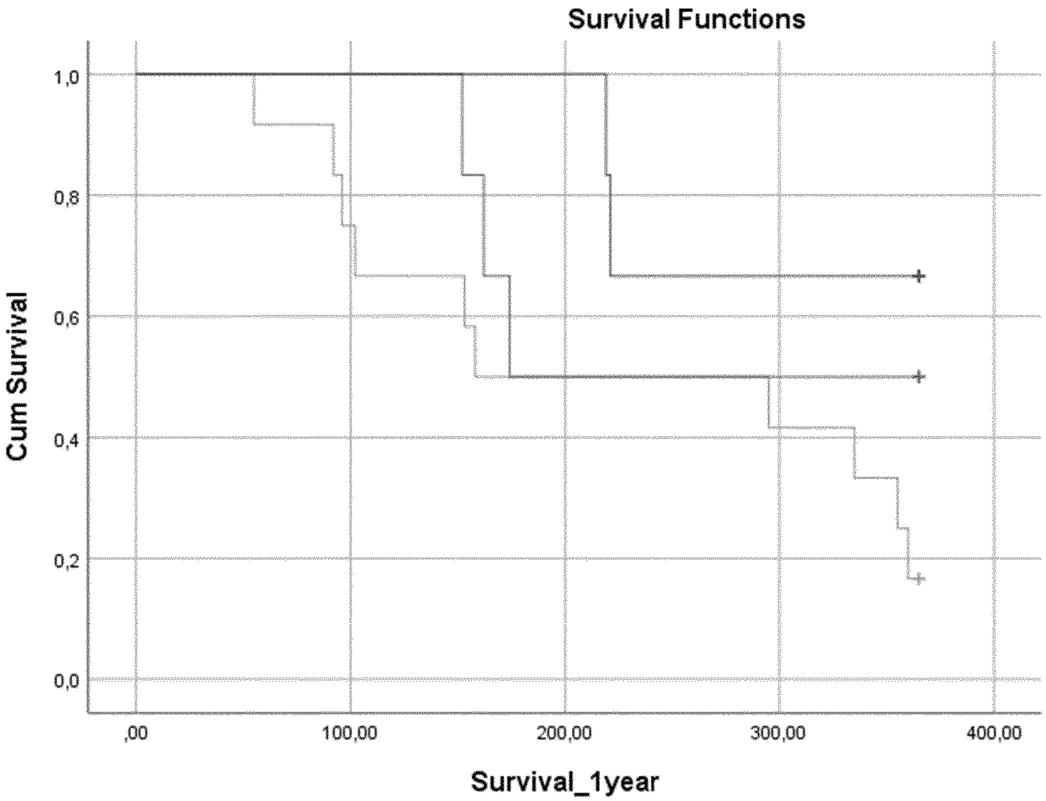
FIG. 9: Cumulative survival over a one year time interval of subjects receiving allogenic FMT from donor 23 (line having the highest endpoint, indicated by a "+" sign, after one year), of subjects receiving allogenic FMT from all other donors (line having the second highest endpoint, indicated by a "+" sign, after one year), and of subjects receiving autologous FMT (line having the lowest endpoint, indicated by a "+" sign, after one year).

In FIG. 9, the cumulative survival of patients receiving allogenic FMT from donor 23 (line having the highest end point after one year) is compared to all other patients, both from the allogenic and the autologous groups (line having the lowest endpoint after one year), and all other patients in the allogenic FMT group (line having an endpoint intermediate both other lines). A large positive effect of FMT from donor 23 can thus be observed (FIG. 9).

Figure 10:
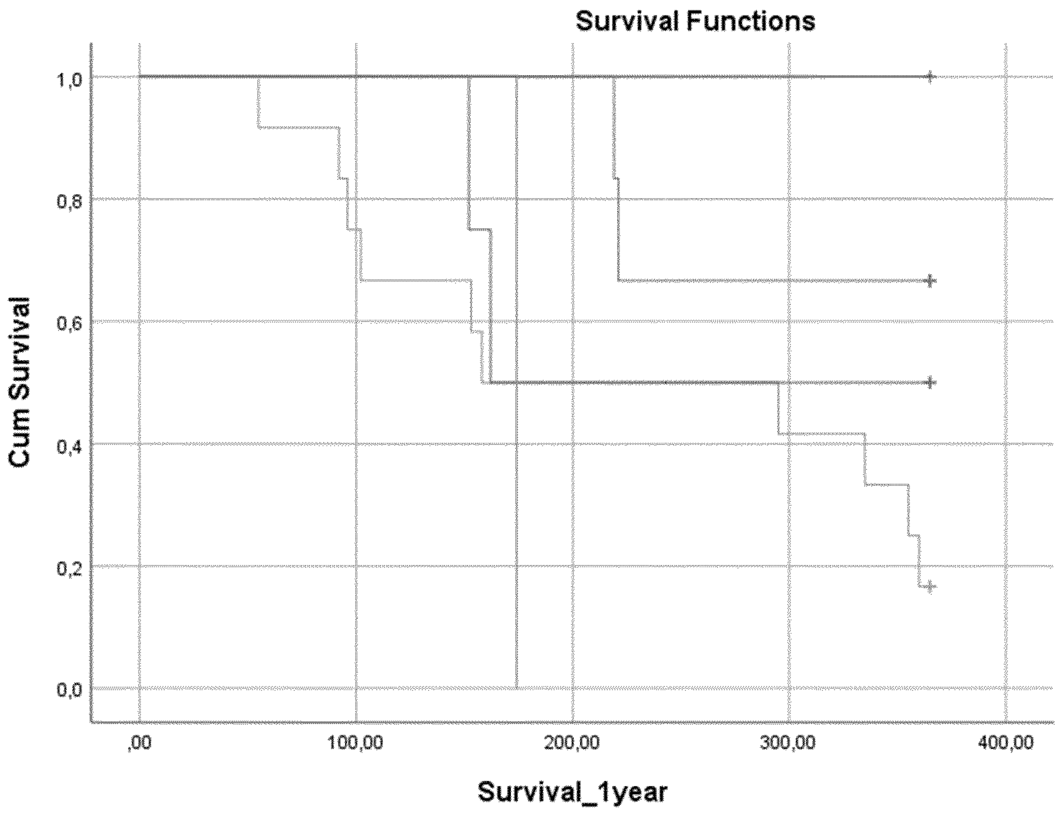
FIG. 10: Cumulative survival over a one year time interval of a subject receiving allogenic FMT from donor 21 (line having the highest endpoint, indicated by a "+" sign, after one year), of subjects receiving allogenic FMT from donor 23 (line having the second highest endpoint, indicated by a "+" sign, after one year), of subjects receiving allogenic FMT from donor 14 (line having the third highest endpoint, indicated by a "+" sign, after one year), of a subject receiving allogenic FMT from donor 22 (line ending at zero before 200 days), and of subjects receiving autologous FMT (line having the lowest endpoint, indicated by a "+" sign, after one year).

FIG. 10 displays the cumulative survival of patients for each specific donor as compared to the autologous FMT group. As can be seen, the sole patient (see Table 5) receiving FMT from donor 21 is still alive after one year (line having the highest endpoint after one year), while the patient receiving FMT from donor 22 has passed away before the one year time point. Four out of six patients who received FMT from donor 23 are still alive after one year (line having the second highest endpoint after one year), and two out of four patients who received FMT from donor 14 are still alive after one year (line having the third highest endpoint after one year). Only two out of twelve patients receiving autologous FMT are still alive after one year.

Factors Influencing Effectiveness of Allogenic FMT

There thus appear to be donor-specific aspect influencing the effectiveness of allogenic FMT. Most preferably, a BMI of FMT donors is above 30. As BMI is not a measure to distinguish between donor 23 and donors 21 and 22, insulin resistance of the donors was quantified.

Insulin resistance (IR) and beta-cell function (β) can be quantified by homeostatic model assessment (HOMA). By using fasting glucose and insulin levels, estimates for insulin resistance (HOMA-IR) and beta-cell function (HOMA-β) can be made. Within the group of patients receiving allogenic FMT, the 6 patients receiving FMT from donor 23 all showed a response. Donor 23 is a healthy young rugby player, while donors 14 and 21 are older and likely to have higher HOMA-IR values. The HOMA-IR value of donor 23 is below 2.5, while the HOMA-IR values of donors 14 and 21 are both above 2.5.

In order to diagnose obesity in athletes, such as rugby players, body fat can be assessed by means of skin-fold measurements or, failing that, by measuring waist circumference to height ratios. An estimated 72% of athletes are wrongly classified as obese by their BMI.

In addition, donor 23 is much younger than donors 21 and 22. There thus appears to be an influence of donor age on the outcome of FMT as well. Preferably, the age of a donor is below 40. Based on donor 23, there appears to be a beneficial effect on patients receiving FMT from donors having low body fat and high muscle strength, in addition to the aforementioned factors.

Example 3

Administration of allogenic fecal matter derived from varying donors to recipients diagnosed with different types of cancer Patients with cancer types as indicated below (recipients) receive allogenic fecal matter by duodenal tube administration after bowel lavage (as in Example 1), according to the following 3 treatment arms:

1. Allogenic fecal matter transplantation from donors having a BMI between 18 and 30 kg/m$^2$ to recipients at 0, 8 and 16 weeks.
2. Allogenic fecal matter transplantation from donors having a BMI of at least 30 kg/m$^2$ to recipients at 0, 8 and 16 weeks.

2a. Allogenic fecal matter transplantation as in treatment arm 2, wherein the donors have a HOMA-IR value below 2.5 mg/dL.

2b. Allogenic fecal matter transplantation as in treatment arm 2, wherein the donors are 40 years or younger.

2c. Allogenic fecal matter transplantation as in treatment arm 2a, wherein the donors do not have metabolic syndrome.

2d. Allogenic fecal matter transplantation as in treatment arm 2c, wherein the donors have a supraspinal skinfold thickness below 36 mm and a waist circumference to height ratio between 0.50 and 0.65 m/m.

TABLE 6

| Treatment scheme | | | | | |
|---|---|---|---|---|---|
| | | Average putative effects perceived by recipients | | | |
| Treatment arm | No. of recipients per disease* | PFS* (months) | Response to chemotherapy | Perceived side effects of chemotherapy | QOL* (0 to 100%) |
| 1 | 4 EC | 24 | Slight improvement | Very severe | 25 |
| | 6 GC | 45 | Slight improvement | Severe | 33 |
| | 3 GEC | 23 | Slight improvement | Very severe | 24 |
| | 2 PC | 9 | No improvement | Very severe | 15 |
| 2 | 5 EC | 28 | Moderate improvement | Moderate | 40 |
| | 5 GC | 52 | Moderate improvement | Mild | 56 |
| | 4GEC | 27 | Moderate improvement | Moderate | 35 |
| | 3 PC | 10 | Moderate improvement | Severe | 26 |
| 2a | 5 EC | 38 | Large improvement | Mild | 47 |
| | 6 GC | 62 | Large improvement | Mild | 63 |
| | 3 GEC | 30 | Large improvement | Mild | 41 |
| | 2 PC | 18 | Large improvement | Mild | 31 |
| 2b | 4 EC | 34 | Large improvement | Mild | 49 |
| | 6 GC | 65 | Large improvement | Mild | 61 |
| | 3 GEC | 30 | Large improvement | Mild | 42 |
| | 3 PC | 16 | Large improvement | Mild | 31 |
| 2c | 4 EC | 35 | Large improvement | Mild | 50 |
| | 6 GC | 61 | Large improvement | Mild | 66 |
| | 4 GEC | 33 | Large improvement | Mild | 49 |
| | 3 PC | 15 | Large improvement | Mild | 31 |

TABLE 6-continued

| Treatment scheme | | | | | |
| --- | --- | --- | --- | --- | --- |
| | | Average putative effects perceived by recipients | | | |
| Treatment arm | No. of recipients per disease* | PFS* (months) | Response to chemotherapy | Perceived side effects of chemotherapy | QOL* (0 to 100%) |
| 2d | 5 EC | 39 | Large improvement | Mild | 53 |
| | 5 GC | 66 | Large improvement | Mild | 68 |
| | 3 GEC | 39 | Large improvement | Mild | 46 |
| | 2 PC | 19 | Large improvement | Mild | 35 |

*PFS: Progression-Free Survival, QOL: Quality of Life, EC: esophageal cancer, GC: gastric cancer, GEC: gastro-esophageal junction cancer, PC: pancreatic cancer.

Similar results for PFS and QOL may be obtained for recipients suffering from cachexia or sarcopenia either with or without diagnosed cancer. Further, it is expected that results similar to the putative effects as shown in table 6 above can be obtained with larger patient cohorts.

REFERENCES

1. Fearon, K. C. & Voss, A. C. Definition of cancer cachexia: effect of weight loss, reduced food intake, and systemic inflammation on functional status and 1-6 (2006).
2. Prado, C. M. et al. Prevalence and clinical implications of sarcopenic obesity in patients with solid tumors of the respiratory and gastrointestinal tracts: a population-based study. Lancet Oncol. 9, 629-635 (2008).
3. World Health Organization. Towards a Common Language for Functioning, Disability and Health ICF. Int. Classif. 1149, 1-22 (2002).
4. Pusuroglu, H. et al. Analiza porównawcza calkowitej liczby leukocytów i określonego typu leukocytów między grupami pacjentów z izolowanym nadciśnieniem skurczowym, nadciśnieniem skurczowo-rozkurczowym i prawidlowym ciśnieniem tętniczym. Kardiol. Pol. 72, 748-754 (2014).
5. Norman, K., Wirth, R., Neubauer, M., Eckardt, R. & Stobäus, N. The bioimpedance phase angle predicts low muscle strength, impaired quality of life, and increased mortality in old patients with cancer. J. Am. Med. Dir. Assoc. 16, 173.e17-173.e22 (2015).

The invention claimed is:

1. A method for treating cachexia in a human patient in need thereof, the method comprising administering allogenic fecal matter to the patient in need thereof, wherein the allogenic fecal matter is obtained from at least one human donor, wherein the at least one human donor has a Body Mass Index (BMI) of at least 30 kg/m$^2$; a Homeostatic Model Assessment of Insulin Resistance (HOMA-IR) of at most 2.5 mg/dL and an age of at most 60 years, wherein the human patient and the human donor are not one and the same.

2. The method according to claim 1, wherein the at least one human donor has a BMI of at least 31 kg/m$^2$.

3. The method according to claim 1, wherein the at least one human donor has a HOMA-IR of at most 2.0 mg/dL.

4. The method according to claim 1, wherein the at least one human donor has an age of at most 40 years.

5. The method according to claim 1, wherein the at least one human donor does not have metabolic syndrome.

6. The method according to claim 1, wherein the cachexia is associated with cancer, congestive heart failure, chronic obstructive pulmonary disease, chronic kidney disease or AIDS.

7. The method according to claim 6, wherein the cachexia is associated with a cancer selected from the group consisting of esophageal cancer, gastric cancer, gastro-esophageal cancer, and pancreatic cancer.

8. The method according to claim 1, wherein the method is for improving response to therapy or reducing therapy side effects.

9. The method according to claim 1, wherein the method is not for increasing body weight or for increasing BMI.

10. The method according to claim 1, wherein the allogenic fecal matter is administered to the human patient's small intestine.

11. The method according to claim 1, wherein the fecal matter is comprised in a liquid medium and does not comprise solids having a diameter of more than 10 μm.

12. The method according to claim 1, wherein the fecal matter is combined with a chemotherapeutic agent.

13. The method according to claim 1, wherein the allogenic fecal matter is comprised in a pharmaceutical composition, a liquid form, a solid dosage form, a capsule, a tablet, or a powder.

14. A method of treating cachexia in a human patient in need thereof comprising administering allogenic fecal matter to the patient in need thereof, wherein the allogenic fecal matter is obtained from at least one human donor who does not have metabolic syndrome, wherein the at least one donor subject has a Body Mass Index (BMI) of at least 34 kg/m$^2$; a HOMA-IR of at most 1.0 mg/dL and an age of at most 25 years, and wherein the cachexia is associated with cancer, congestive heart failure, chronic obstructive pulmonary disease, chronic kidney disease, or AIDS and wherein the human patient and the human donor are not one and the same.

15. The method according to claim 14, wherein the allogenic fecal matter is administered to the human patient's duodenum.

* * * * *